(12) United States Patent
Gehling et al.

(10) Patent No.: US 8,113,207 B2
(45) Date of Patent: Feb. 14, 2012

(54) SELF-CONFORMING SOUND ATTENUATION EARPLUG

(75) Inventors: Steven Craig Gehling, Cumming, GA (US); Waihong Leong, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 127 days.

(21) Appl. No.: 12/229,475

(22) Filed: Aug. 22, 2008

(65) Prior Publication Data

US 2010/0043806 A1 Feb. 25, 2010

(51) Int. Cl.
*A61F 11/00* (2006.01)
*A61B 7/02* (2006.01)

(52) U.S. Cl. ........................ 128/864; 181/135
(58) Field of Classification Search .................. 128/846, 128/857, 864; 181/135, 134, 130, 129, 133
See application file for complete search history.

(56) References Cited

U.S. PATENT DOCUMENTS

| | | |
|---|---|---|
| 3,618,600 A | 11/1971 | Douglass |
| 3,736,929 A | 6/1973 | Mills |
| 3,768,470 A | 10/1973 | Leight |
| 3,771,521 A | 11/1973 | Kittredge |
| 3,782,379 A | 1/1974 | Lampe |
| 3,800,791 A | 4/1974 | Visor |
| 3,811,437 A | 5/1974 | Gardner, Jr. |
| 3,872,559 A | 3/1975 | Leight |
| 3,881,570 A | 5/1975 | Lewis |
| 3,896,801 A | 7/1975 | Grout |
| 3,915,166 A | 10/1975 | McCrink |
| 4,053,051 A | 10/1977 | Brinkhoff |
| 4,060,080 A | 11/1977 | Akiyama |
| 4,089,332 A | 5/1978 | Rose |
| 4,094,315 A | 6/1978 | Leight |
| 4,143,657 A | 3/1979 | Takeda |
| 4,160,449 A | 7/1979 | Wade |
| 4,193,396 A | 3/1980 | Wacker |

(Continued)

FOREIGN PATENT DOCUMENTS

BE 886002 A 2/1981

(Continued)

OTHER PUBLICATIONS

American Society for Testing Materials (ASTM) Designation: D1735-02, "Standard Practice for Testing Water Resistance of Coatings Using Water Fog Apparatus," pp. 1-3, published Oct. 2002.

(Continued)

*Primary Examiner* — Patricia Bianco
*Assistant Examiner* — Tarla Patel
(74) *Attorney, Agent, or Firm* — Nancy M. Klembus; Michael Bendel

(57) ABSTRACT

A self-conforming sound attenuation earplug for location in an ear canal. The earplug includes a stem. At least one support is joined with the stem and located between the stem ear end and the stem user end, and extends radially outward from the stem. A shell is made of a deformable-resilient shell material and has a tapered exterior that increases in circumference when moving from the stem ear end to the stem user end. The shell engages at least a portion of the support and engages at least a portion of the stem located between the stem ear end and the stem user end. At least a portion of the support is free from contact with the shell and the support material is a different type of material than the shell material.

13 Claims, 3 Drawing Sheets

U.S. PATENT DOCUMENTS

| | | | |
|---|---|---|---|
| 4,215,683 A | 8/1980 | Lundin et al. | |
| 4,253,452 A | 3/1981 | Powers et al. | |
| 4,314,553 A | 2/1982 | Westerdal | |
| 4,344,425 A | 8/1982 | Strauss | |
| 4,434,794 A | 3/1984 | Leight | |
| 4,459,247 A | 7/1984 | Rothemund | |
| 4,461,290 A | 7/1984 | Gardner, Jr. et al. | |
| 4,498,469 A | 2/1985 | Csiki | |
| 4,582,053 A | 4/1986 | Wilson | |
| 4,702,238 A | 10/1987 | Scott | |
| 4,774,938 A | 10/1988 | Leight | |
| 4,806,186 A | 2/1989 | Sirkin et al. | |
| 4,867,149 A | 9/1989 | Falco | |
| 4,896,679 A | 1/1990 | St. Pierre | |
| 4,936,411 A | 6/1990 | Leonard | |
| 5,044,463 A | 9/1991 | Carr | |
| 5,074,375 A | 12/1991 | Grozil | |
| 5,113,967 A | 5/1992 | Killion et al. | |
| 5,119,833 A | 6/1992 | Powers | |
| 5,153,387 A | 10/1992 | Zwislocki et al. | |
| 5,188,123 A | 2/1993 | Gardner, Jr. | |
| 5,249,309 A | 10/1993 | Berg et al. | |
| 5,452,731 A | 9/1995 | Dickman | |
| 5,467,784 A | 11/1995 | Mobley et al. | |
| 5,483,027 A | 1/1996 | Krause | |
| 5,557,077 A | 9/1996 | Berg | |
| 5,573,015 A | 11/1996 | Williams | |
| 5,581,821 A | 12/1996 | Nakano | |
| 5,668,354 A | 9/1997 | Falco | |
| 5,711,313 A | 1/1998 | Fleming | |
| 5,727,566 A | 3/1998 | Leight | |
| 5,811,742 A | 9/1998 | Leight | |
| 5,936,208 A | 8/1999 | Hamery | |
| 5,957,136 A | 9/1999 | Magidson et al. | |
| 5,988,313 A | 11/1999 | Håkansson | |
| 6,006,857 A | 12/1999 | Leight et al. | |
| 6,082,485 A | 7/2000 | Smith | |
| 6,105,715 A | 8/2000 | Knauer | |
| 6,129,175 A | 10/2000 | Tutor et al. | |
| 6,148,821 A | 11/2000 | Falco | |
| 6,241,041 B1 | 6/2001 | Leight | |
| 6,241,042 B1 | 6/2001 | Falco | |
| 6,256,396 B1 | 7/2001 | Cushman | |
| 6,264,870 B1 | 7/2001 | Håkansson | |
| 6,286,622 B1 | 9/2001 | Tiemann | |
| 6,364,052 B1 | 4/2002 | McLean | |
| 6,408,981 B1 | 6/2002 | Smith et al. | |
| 6,425,398 B1 | 7/2002 | Hirshfeld | |
| 6,427,800 B1 | 8/2002 | Hiselius et al. | |
| 6,484,726 B1 | 11/2002 | Remer et al. | |
| D472,627 S | 4/2003 | Falco | |
| 6,568,394 B2 | 5/2003 | Falco | |
| 6,568,395 B2 | 5/2003 | Tiemens | |
| 6,659,103 B2 | 12/2003 | Tiemens | |
| 6,691,822 B2 | 2/2004 | Meussen et al. | |
| 6,695,093 B1 | 2/2004 | Falco | |
| 6,761,173 B1 | 7/2004 | Kuno et al. | |
| 6,920,956 B1 | 7/2005 | Falco | |
| 6,938,622 B2 | 9/2005 | Huang | |
| 6,981,504 B2 | 1/2006 | Jenkins, Jr. | |
| 7,025,061 B2 | 4/2006 | Haussmann | |
| 7,096,872 B2 | 8/2006 | Ligon, Sr. et al. | |
| 7,107,993 B2 | 9/2006 | Magidson | |
| 7,475,686 B2 | 1/2009 | Knauer et al. | |
| 2002/0124851 A1 | 9/2002 | Knauer et al. | |
| 2002/0153192 A1 | 10/2002 | Falco et al. | |
| 2003/0029459 A1 | 2/2003 | Tiemens | |
| 2003/0075185 A1 | 4/2003 | Ulbrich | |
| 2003/0172938 A1* | 9/2003 | Falco | 128/864 |
| 2004/0045558 A1 | 3/2004 | Taylor et al. | |
| 2004/0069310 A1 | 4/2004 | Falco | |
| 2004/0129276 A1 | 7/2004 | Kuno et al. | |
| 2005/0020858 A1 | 1/2005 | Wu et al. | |
| 2005/0039761 A1 | 2/2005 | Jenkins | |
| 2005/0056289 A1 | 3/2005 | Jenkins et al. | |
| 2005/0094835 A1 | 5/2005 | Doty | |
| 2005/0135650 A1 | 6/2005 | Berger | |
| 2005/0229938 A1 | 10/2005 | Jenkins | |
| 2005/0274568 A1 | 12/2005 | Falco et al. | |
| 2006/0081415 A1 | 4/2006 | Knauer et al. | |
| 2006/0118124 A1 | 6/2006 | Woo et al. | |
| 2006/0213524 A1 | 9/2006 | Woo et al. | |
| 2006/0272649 A1 | 12/2006 | Fleming | |
| 2006/0278468 A1 | 12/2006 | Bruck | |
| 2007/0221232 A1 | 9/2007 | Jenkins | |
| 2008/0147025 A1 | 6/2008 | Van Gompel et al. | |
| 2008/0314393 A1* | 12/2008 | Purcell et al. | 128/865 |
| 2009/0095566 A1 | 4/2009 | Leong et al. | |

FOREIGN PATENT DOCUMENTS

| | | |
|---|---|---|
| DE | 02 68 345 C1 | 1/1900 |
| EP | 0 036 422 B1 | 8/1983 |
| EP | 0 059 912 B1 | 2/1985 |
| EP | 0 108 728 B1 | 5/1988 |
| EP | 0 298 956 B1 | 8/1990 |
| EP | 0 244 979 B1 | 9/1990 |
| EP | 0 487 716 B1 | 9/1995 |
| EP | 1 192 920 A1 | 4/2002 |
| EP | 0 786 241 B1 | 7/2003 |
| EP | 0 836 840 B1 | 12/2003 |
| EP | 1 006 968 B1 | 1/2004 |
| EP | 1 276 443 B1 | 3/2006 |
| EP | 1 629 809 A1 | 3/2006 |
| JP | 2004-187745 A | 7/2004 |
| WO | WO 91/03218 A1 | 3/1991 |
| WO | WO 95/15067 A1 | 6/1995 |
| WO | WO 98/07296 A1 | 2/1998 |
| WO | WO 98/25558 A1 | 6/1998 |
| WO | WO 00/45760 A1 | 8/2000 |
| WO | WO 01/76519 A1 | 10/2001 |
| WO | WO 02/09614 A2 | 2/2002 |
| WO | WO 02/15829 A1 | 2/2002 |
| WO | WO 02/43633 A1 | 6/2002 |
| WO | WO 03/063744 A2 | 8/2003 |
| WO | WO 2004/028422 A1 | 4/2004 |
| WO | WO 2004/039296 A2 | 5/2004 |
| WO | WO 2004/066895 A1 | 8/2004 |
| WO | WO 2004/075774 A2 | 9/2004 |
| WO | WO 2004/100608 A2 | 11/2004 |
| WO | WO 2005/025796 A1 | 3/2005 |
| WO | WO 2005/120131 A2 | 12/2005 |
| WO | WO 2005/122981 A1 | 12/2005 |
| WO | WO 2006/078767 A1 | 7/2006 |
| WO | WO 2006/084172 A1 | 8/2006 |

OTHER PUBLICATIONS

American Society for Testing Materials (ASTM) Designation: D2856-94, "Standard Test Method for Open-Cell Content of Rigid Cellular Plastics by the Air Pycnometer," pp. 143-148, published May 1994.

American Society for Testing Materials (ASTM) Designation: D3574-05, "Standard Test Methods for Flexible Cellular Materials—Slab, Bonded, and Molded Urethane Foams," pp. 1-25, published Aug. 2005.

"How Foam Firmness Affects Performance," *In•Touch®—Information on Flexible Polyurethane Foam*, vol., No. 3, published by Polyurethane Foam Association, Jul. 1994, pp. 1-3.

"Pura-Cones™ Foam Earplugs," Moldex-Metric, Inc., Culver City, CA, Internet web page "http://www.moldex.com/foamplugprod/puracones.htm", viewed and printed Jun. 20, 2007, 2 pgs.

"Traffic Cones® Foam Earplugs," Moldex-Metric, Inc., Culver City, CA, Internet web page "http://www.moldex.com/foamplugprod/trafficcones.htm", viewed and printed Jun. 20, 2007, 2 pgs.

Bjorn, Valerie S. et al., "U.S. Navy Flight Deck Hearing Protection Use Trends: Survey Results," *New Directions for Improving Audio Effectiveness*, Meeting Proceedings RTO-MP-HFM-123, Paper 1, 2005, pp. 1-1 through 1-20.

* cited by examiner

SELF-CONFORMING SOUND ATTENUATION EARPLUG

BACKGROUND OF THE INVENTION

The present invention relates generally to devices for location in an ear canal, and more particularly to earplugs that are insertable, self-conforming and used for noise reduction, e.g., sound attenuation.

The need for adequate hearing protection in noisy environments has long been recognized among those concerned with health and safety issues, and much effort has gone into providing such protection. However, most experts in this field would acknowledge that this effort has not been completely successful. Protective devices have proliferated yet remain needing in performance, particularly in terms of a comfortable fit over a longer period of time (e.g., at least 4 hours). Workers in noisy environments who should use these devices often do not, or use them only under duress from their employers, and then do so improperly because they value comfort over a proper, likely uncomfortable, fit. Individuals that work in noisy environments rarely understand that the effects of noise exposure are not limited to the moment but are cumulative as well. The lack of worker compliance with safety rules is exacerbated by the fact that currently available hearing protection devices are often uncomfortable, clumsy to use, and/or perform less than optimal due to improper insertion in the ear canal. Additionally, human ear canal sizes vary from about 7 to about 8 millimeters in diameter for "small" canals, to about 9 to about 10 millimeters in diameter for "medium" canals, to about 11 to about 12 and as much as about 14 millimeters for "large" canals. Fortunately, as hearing protection devices become more comfortable and/or fit better across a broader range of canal sizes, worker compliance with their use should also improve.

For example, existing disposable roll-down foam earplugs can be uncomfortable when worn over longer periods of time, are difficult to properly insert, and/or do not readily stay in place for a longer period of time. Common disposable foam earplugs require the user to compress the volume of the plug and insert it into the ear canal where it then attempts to re-expand. This method can cause discomfort for people with ear canals that are not the largest ones contemplated for that earplug's intended use, in that the more compressed the earplug in an ear sized smaller than "large", the greater the earplug's exerted outward force toward re-expansion. Such a roll-down type earplug may be found, for example, in U.S. Pat. No. 6,105,715 to Knauer.

Further, existing disposable foam earplugs require the user to roll the foam between their fingers to compress the foam to a sufficient size for proper insertion. If this step is not done, or is done insufficiently, the earplug is often inserted improperly (i.e., usually meaning not inserted enough into the ear canal) so as to not provide optimal protection (i.e., not optimal often being as little as 25% of the earplugs' advertised Noise Reduction Rating ("NRR") as determined by industry standards). And, even when the earplug is initially inserted properly, it is common for workers in a work environment that requires continuous earplug use to experience discomfort from the pressure exerted from the residual expansion forces of the rolled earplug. The discomfort is sometimes relieved by the partial removal of the earplug from the ear canal, thereby compromising the sound attenuating protection of the device. Also, if the user has dirty hands when compressing the earplug, dirt and/or germs are then put into the ear canal with the inserted earplug.

As with roll-down type earplugs, push-in type earplugs attenuate sound by causing an occlusion within the ear canal, thus obstructing the passage of sound therethrough. Push-in type earplugs generally comprise an attenuating annular portion and a rigid to semi-rigid stem portion typically extending therefrom or embedded therein and used as an insertion means. The sound attenuating portion is typically of a soft compressible material. The rigid to semi-rigid portion may be composed of any material with sufficient rigidity as required to overcome the insertion pressure of the earplug, and is often formed of the same material in one molding process step. To insert the push-in type earplug, the user grasps the rigid/semi-rigid portion (or an end of the earplug proximate thereto), positions the earplug proximate the ear canal opening, and inserts the sound attenuating portion into the canal by pushing with the rigid/semi-rigid portion. The sound attenuating portion compresses, as necessary, upon entry into the ear canal and is held therein by a friction fit, occluding the canal and providing sound attenuation. Such a push-in type earplug may be found, for example, in U.S. Pat. Nos. 4,867,149 and 5,188,123 to Falco and Gardner Jr., respectively.

Push-in type earplugs are considered by many to provide easier insertion than other types of plugs. As discussed above, the wearer simply grasps the rigid or semi-rigid portion (or the end of the earplug proximate thereto) and inserts the sound attenuating portion at the opposite end into the ear canal, lodging the earplug therein and, hence, occluding the canal. However, while allowing a simplistic insertion, the push-in type ear plug typically does not yield the higher attenuations often provided by roll-down type earplugs. This may be because the push-in plug typically has a less surface area contacting the ear canal when inserted therein, or perhaps because the push-in plug wrinkles or folds during insertion creating leaks, or further, because the push-in plug does not stay firmly in place during use and backs slightly out of the ear canal.

Therefore, existing roll-down and push-in type earplug materials and constructions alone do not have the ability to simultaneously accommodate each of: adequate insertion means, comfortable fit and sound attenuation. Accordingly, a hearing protection device is needed which is easy to insert, comfortable to the user during a longer period of use, and provides desired sound attenuation. The applicants have surprisingly invented such a device, as discussed further herein.

SUMMARY OF THE INVENTION

Various definitions used throughout the specification and claims are provided first, followed by a description of various aspects of the invention.

As used herein, "deformable-resilient" means the property of a material or composite material that permits it to be deformed in size and/or shape: (i) to 70% or less of its original size and/or shape by a sufficiently large force applied to cause deformation and (ii) then such recovers at least about 80% of its original size and shape no later than two minutes after removal of the force causing the deformation.

As used herein, "different type of material" means one material that differs from a second material in (i) chemical composition or formulation or formation process which (ii) causes a difference in performance of the one material from the second material when the two materials are formed in the same size and shape as each other and they are performance tested under the same conditions.

As used herein, "same type of material" means one material that is the same as a second material in (i) chemical composition and formulation and formation process such that (ii) there is no difference in performance of the one material from the second material when the two materials are formed in the same size and shape as each other and they are performance tested under the same conditions.

As used herein, "Softness Rating" means the Compression Force Deflection ("CFD") value for a flexible cellular material as determined using the standardized test method described in ASTM-D-3574, American Society for Testing and Materials, 2005, Test $C_1$—Compression Force Deflection Test—25%. The flexible cellular material used to construct the shell material of the invention is made into 3 test samples, each being a flat piece of foam having dimensions of 50 millimeters wide by 50 millimeters long by 25 millimeters thick. Each sample is tested according to the test method to determine its final force in newtons and its equivalent measures in other scales, at 25% deflection. In the test, each sample is twice preflexed to 75% of the specimen's thickness at 250 millimeters/min, and then allowed to rest with the flex force removed, for six minutes. For the measured test then, the preflexed sample is indented at 50 millimeters/min to 25% of its total thickness and the force in newtons observed at that deflection after 60 seconds. The average of the force values for the three samples is the Softness Rating for that shell material.

In one aspect of the present invention, there is provided a self-conforming sound attenuation earplug for location in an ear canal. The earplug includes a stem made of a stem material and having a stem ear end and an opposite stem user end. At least one support is joined with the stem and made of a support material and has at least a part of the support located between the stem ear end and the stem user end, where the support extends radially outward from the stem. A shell is made of a deformable-resilient shell material and has a tapered exterior that increases in circumference when moving from the stem ear end to the stem user end. The shell engages at least a portion of the support and engages at least a portion of the stem located between the stem ear end and the stem user end. At least a portion of the support is free from contact with the shell and the support material is a different type of material than the shell material.

Other features of the invention relate to particular configurations and characteristics of the stem, the support and the shell, each alone and in relation to each other. Still other features of the invention will be in part apparent and in part pointed out hereinafter as well as better understood by practice of the invention.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the earplug for location in an ear canal that is the present invention.

BRIEF DESCRIPTION OF THE DRAWINGS

Corresponding reference characters indicate corresponding parts throughout the drawings.

DETAILED DESCRIPTION

Figure 3:
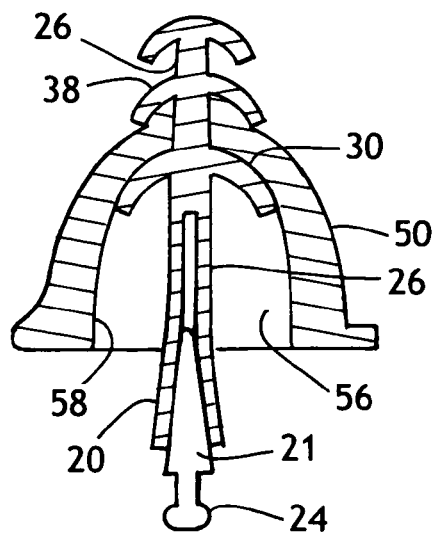
FIG. 3 is a cross-sectional view of an alternative embodiment of the present invention.
Figure 10:
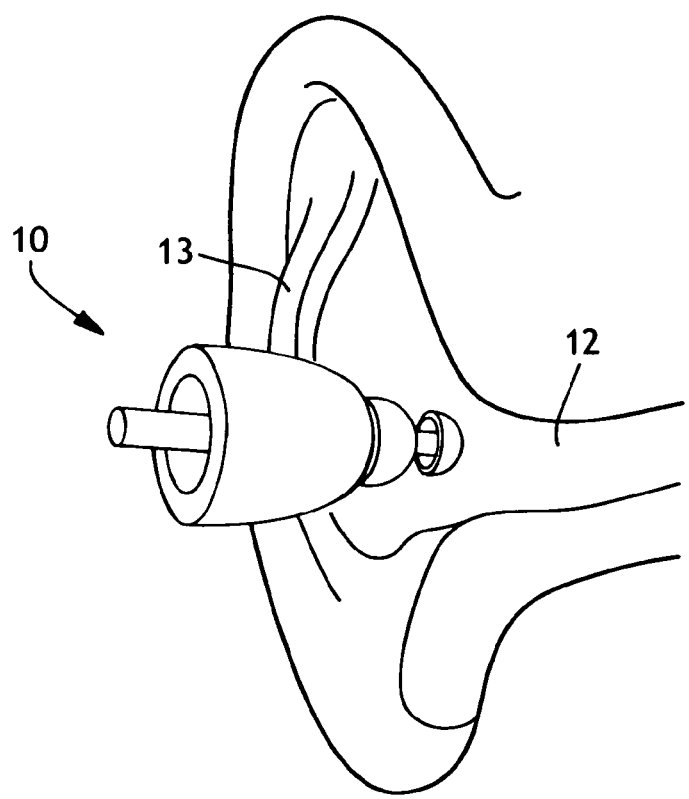
FIG. 10 is a perspective view of the earplug in FIG. 1 as it is about to be inserted in an ear canal.

Referring now to the drawings, there is depicted a self-conforming sound attenuation earplug 10 for location in an ear canal 12. Particularly in FIG. 10, there is seen outer ear 13 joined to the portion of the ear canal 12 through which the earplug 10 is inserted for use, and where the ear drum (not seen) is located at the other end of the ear canal spaced from the earplug when inserted into the ear canal. Earplug 10 includes a stem 20, a support 30, and a shell 50. Stem 20 is made of a stem material and includes a stem ear end 22 and an opposite stem user end 24. Stem 20 may include a stem extension 21 (i.e., FIGS. 3, 5, and 7), for example, to aid in insertion of earplug 10 or locating with a mating device (not shown). Extension 21 may be integral with stem 20, formed independent of stem 20 and then joined together, be a male engagement end (as shown) which plugs into a mating female member (e.g., an ear clip or an ear muff, not shown), or be a female engagement end which plugs into a mating male member. Extension 21 and stem 20 may be made of the same or a different type of material. Stem user end 24 may be bulbous or have other contours or shape to assist with gripping the same.

At least one support 30 is joined with stem 20, and advantageously, two, three, four, or more supports. Support 30 is made of a deformable-resilient support material, and at least a part of the support is located between the stem ear end 22 and the stem user end 24, relative to a side portion of the stem along the stem longitudinal axis. The support extends radially outward from the stem. Support 30 and stem 20 could be formed together of one material, or formed of separate materials that are sequentially formed together, or formed separately and then joined together by any conventional means, such as by, adhesive, chemical, heat, or other similarly resulting mechanical bonded relationship.

The shell 50 has a shell ear end 52, an opposite shell user end 54, is made of a deformable-resilient shell material, and has a tapered exterior that increases in circumference when moving from the stem ear end to the stem user end. The shell engages at least a portion of support 30 and engages at least a portion of stem 20 located between stem ear end 22 and stem user end 24. At least a portion of the support is free from contact with shell 50 and the support material is a different type of material than the shell material.

The following two features of the earplug, in combination with other requirements of the invention as discussed herein, are critical to it achieving its advantageous use over existing in-ear located earplug devices, and in particular attaining the proper balance of fit, comfort and sound attenuation, for enhanced user compliance over longer periods of time. First, the support material and the shell material are each a deformable-resilient material. And second, the shell and the support are composed of a different type of material. Additionally, but not required, the shell and the support can be formed independent of one another to gain another advantage for the earplug.

Without being limited to a theory of understanding, these combined features allow each of the shell and the support to do what they do best, and not make one perform a contradictory role. The applicants have inventively discovered that the ability to comfortably and effectively seal the ear canal with a hearing protection device is related to the ability (i) to keep the earplug surface in continuous contact with the ear canal as the earplug is reduced in size during insertion and (ii) to conform the earplug surface to the irregularly shaped ear canal. The resistance to deformation by the earplug will determine how much force is therefore generated from the dimensional reduction in at least a portion of the earplug shape and/or size as it is inserted into the ear canal. The resistance to deformation is due to the mechanical properties of the earplug material (e.g. durometer, Softness Rating, and/or density) as well as the physical cross sectional shape of the earplug components.

More specifically, and as embodied in the present invention like never before possible, shell 50 can now more so operate as a soft, comfortable material that itself exerts more limited outward pressure on ear canal 12, thereby enabling it to be tailored to addressing the comfort needs of earplug 10, while also taking advantage of the sound attenuation properties of the shell material. For example, shell 50 can help to disperse the local forces of the adjacent support over a broader area thus minimizing the actual force transmitted by the support on any particular point of the ear canal. Also, shell 50 can serve as a cushion against the ear canal which provides comfort for the earplug that is resting against the ear canal over longer periods of use. Still further, shell 50 can act as a gap filler within the ear canal to create a better seal between the earplug and the ear canal.

Complementarily, support 30 made of deformable-resilient material now more so operates as a supportive member to the earplug. The support 30 provides additional shape integrity for the shell, and through this the radially outward force of the support enables a more consistent force profile to the overall earplug both before and when located in ear canal 12. This can also enhance sealing of the support and shell, respectively, against the ear canal when in the ear canal, thereby enabling it to be tailored to addressing the fit needs of earplug 10 in a more comfortable way.

Figure 4:
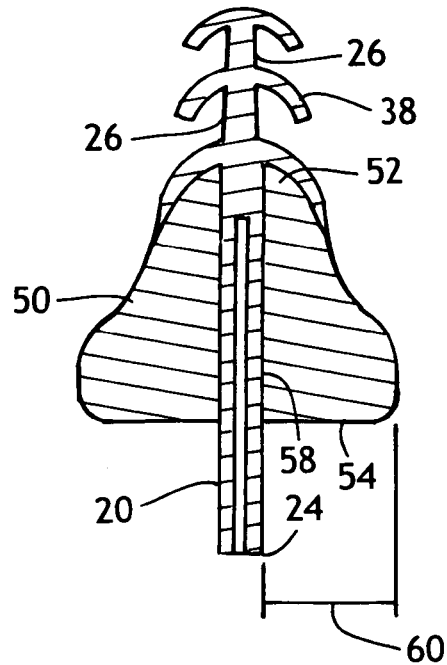
FIG. 4 is a cross-sectional view of an alternative embodiment of the present invention.
Figure 5:
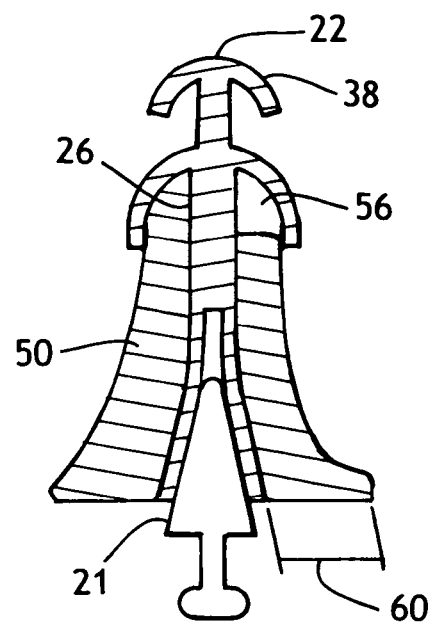
FIG. 5 is a cross-sectional view of an alternative embodiment of the present invention.
Figure 6:
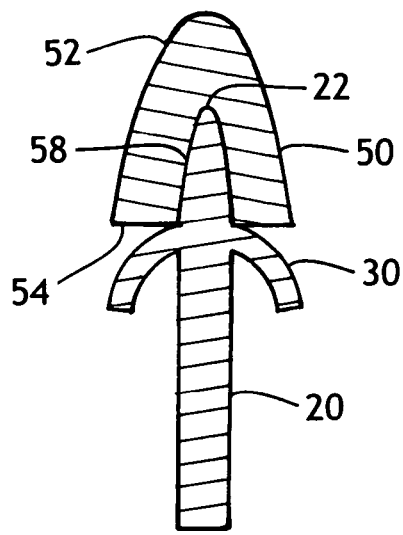
FIG. 6 is a cross-sectional view of an alternative embodiment of the present invention.
Figure 8:
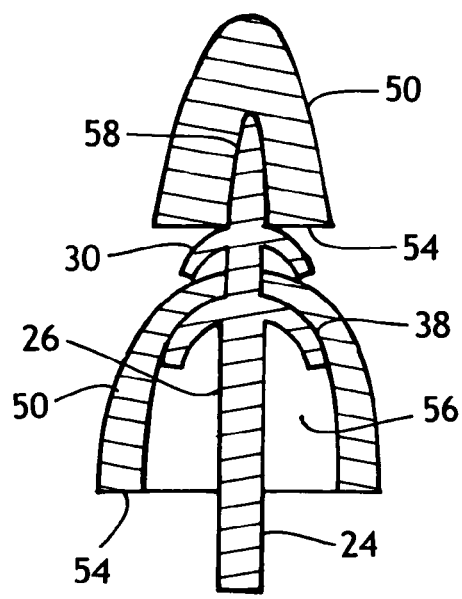
FIG. 8 is a cross-sectional view of an alternative embodiment of the present invention.
Figure 9:
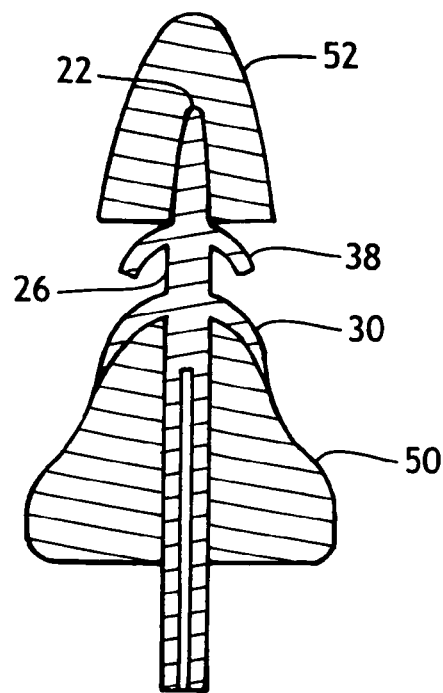
FIG. 9 is a cross-sectional view of an alternative embodiment of the present invention.

Further in this regard, though not required, there are other ways to enhance the just discussed features. For example, a space 56 can be formed between an inner circumference 58 of the shell and an outer circumference 26 of the stem, e.g., FIGS. 2, 3, 5 and 8. As still other examples, there is the positioning of support 30 and second support 38 relative to stem 20 and shell 50. As seen in FIGS. 4, 5 and 9, shell 50 may be located between support 30 and stem user end 24. As seen in FIGS. 8 and 9, there may be two shells 50.

As seen in FIGS. 1-5 and 7-9, at least a second support 38 may be joined with stem 20 and extend radially outward from the stem. The second support may be located between shell 50 and stem ear end 22. Additionally, and still referring to FIGS. 1-5 and 7-9, at least a portion of second support 38 may be free from contact with shell 50. Alternatively, and referring to FIGS. 2, 3 and 8, the shell may be located between support 30 and second support 38.

As seen in FIGS. 1-5 and 7-9 again, at least a second support 38 may be joined with stem 20 where the second support is located between support 30 and stem ear end 24. Additionally, and referring to FIGS. 4 and 5, the second support may be completely free from contact with shell 50.

Figure 7:
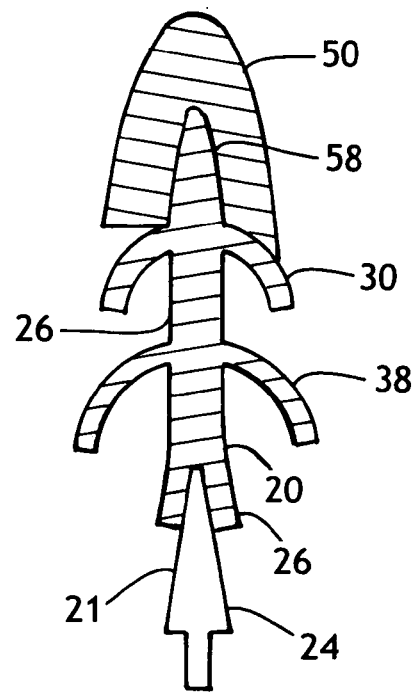
FIG. 7 is a cross-sectional view of an alternative embodiment of the present invention.

As seen in FIG. 7, at least a second support 38 may be joined with the stem where the second support is located between support 30 and stem user end 24. Additionally, second support 38 may be completely free from contact with the shell. Additionally and/or alternatively, shell 50 may be located between support 30 and stem ear end 24.

FIGS. 5 and 7 depict, for illustration purposes, alternative features of a shell 50 being non-symmetrical, e.g., the left side of shell 50 versus the right side of shell 50. Most often, however, shell 50 will be symmetrical, i.e., have either a space 56 all around stem 20 below support 30 (FIG. 5, right side depiction of shell 50), or no space below support 30 (FIG. 5, left side depiction of shell 50), or more fully engaging support 30 all around stem 20 (FIG. 7, right side depiction of shell 50), or less fully engaging support 30 all around stem 20 (FIG. 7, left side depiction of shell 50).

Referring to FIGS. 8 and 9, alternative embodiments are seen with a second shell 50 made of a deformable-resilient second shell material and having a tapered exterior that increases in circumference when moving from the stem ear end to the stem user end. The second shell, may, but need not, engage at least a portion of the stem and may, but need not, be separated from the shell. More particularly, if desired, the second shell 50 may be separated from the shell by at least one support 30 between the second shell and the shell. Alternatively, or additionally, second shell material may be a different type of material than the shell material, or they could be made of the same type of material.

The shell material may have a shell Softness Rating that is between about 0.5 N [0.0020 Kg/cm$^2$] and 10.0 N [0.0407 Kg/cm$^2$]. Advantageously, though not required, the Softness Rating could be, in order of increased softness (and thus preference), between about 2.0 N [0.0081 Kg/cm$^2$] and 8.0 N [0.0326 Kg/cm$^2$], and between about 3.0 N [0.0122 Kg/cm$^2$] and 7.0 N [0.0285 Kg/cm$^2$]. Through each of these additional features, the shell and support combination can provide even better customized sealing of the earplug against the ear canal and enhance fit, while also allowing the support and shell to address comfort needs.

Figure 1:
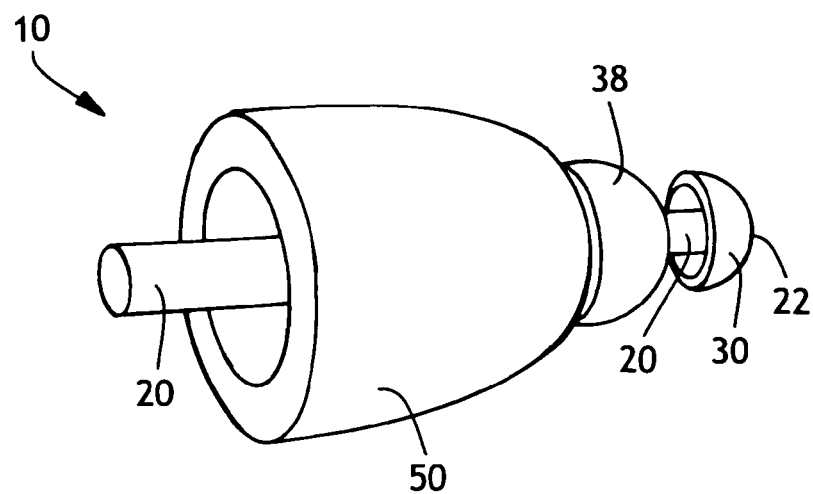
FIG. 1 is a perspective view of the present invention.
Figure 2:
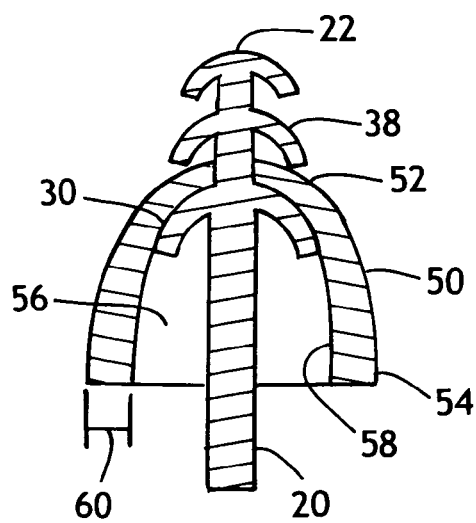
FIG. 2 is a cross-sectional view of the earplug in FIG. 1.

The earplug may include features related to the shell thickness which can provide additional comfort when inserting and/or using earplug 10. Referring to FIG. 2, for example, at least one of the support member and the shell member may have a portion that is a continuous annular cross section ring positioned around and orthogonal to the stem longitudinal axis. When the shell includes such a ring, i.e., the wall of the shell located any where between the shell user end and the shell ear end, it may have a radial thickness 60 between about 1 millimeter and 8 millimeters, more advantageously between about 2 millimeters and about 5 millimeters.

In other aspects of the invention there is provided various configurations for support 30. As seen in all drawings, support 30 can be a continuous cup-shaped member. Further, support 30 can be a continuous cup-shaped member where the cup-shaped member has a spherical cross-sectional shape.

The support(s) can be made of a homogeneous material or a composite material, may include one or more layers, and some or all of the supports may be of the same type of material. Such materials may be polyurethane santoprene, polyethylene, or polypropylene, or other thermo-plastic elastomer polymeric or other rubber or deformable-resilient material having a Shore A Durometer Hardness value between about 10 and about 90, and with a material thickness between about 0.20 millimeters and about 5 millimeters.

The stem may be made of the same type of materials as used for the support, for example, being composed of a deformable-resilient material having a shore A Durometer hardness value between about 10 and about 90, and with a stem material diameter between about 2 millimeters and about 8 millimeters.

The shell may be made of polyurethane santoprene, polyethylene, or polypropylene, or other thermo-plastic elastomer polymeric materials, hydro-entangled materials, air-entangled materials, paper materials such as tissue, toilet paper, or paper towels, waxed paper materials, coform materials, film or plastic materials such as those used to wrap food, or any other generally soft and pliable material that has the desired characteristics of the present invention. Furthermore, laminated or plied together multi-layer materials of two or more layers of any of the preceding materials may be employed. For example, the shell can be made of visco-elastic foam material which has various material properties. The density of the shell material can be about 4 to 20 lbm/ft$^3$ as measured by ASTM D-3574-05. More desirably, the density of the shell material can be about 5 to 12 lbm/ft$^3$. The foam can be further described by the cell size and desirably can have a minimum cell size >80 pores per inch and more desirably >100 pores per inch. The recovery time for the foam material can be desirably between 2 and 2,000 seconds, but more desirably between 120 and 1,600 seconds, as measured by a standard test for the recovery time that is found in ASTM 3574-05, previously cited. The humidity absorption of the foam can be desirably <20% and more desirably <5%, as measured by standard test methods such as found in ASTM D1735.

Other aspects of the invention concern the construction of the shell and the support relative to one another. For example, the stem and the support may be composed of the same type of material. Alternatively, the stem and the support can be each formed independently and then joined together in a fitted relationship.

In practice, earplug 10 may be used as follows. The user grasps the stem user end 24 (e.g., by a user's thumb and/or finger(s) or the like) and then locates the stem ear end adjacent the user's outer ear 13. The user then gently pushes the earplug into the ear canal 12 until is fits snuggly and yet is comfortable. So positioned in the ear canal, the earplug can perform sound optimization such as noise reduction for the user, as desired. In particular, the final in-ear position is determined by the user's particular ear canal shape and size and is therefore self-conforming and customizable each time it is used. For removal, the user simply pulls the earplug out of their ear, with or without a slight twisting of the stem to aid in more gentle removal. Also, with the features of the present invention it is made of sufficiently substantial materials and design so as to allow for multiple uses, if desired.

While not required, it may be advantageous for sound enhancement, e.g., not only taking advantage of sound reduction capabilities but also hearing aid type capabilities. In this way, earplug 10 can be configured (not shown) to locate a microphone or the like in earplug 10 and help bring desired sound into the ear canal and/or locate a microphone in the ear canal better, e.g., via stem 20 and/or support 30.

For a discussion of additional optional features for use with the invention, reference is made to assignee's prior filed application, of the same title, and having U.S. Ser. No. 11/821,390 of Ricky W. Purcell et al. filed Jun. 22, 2007, and assignee's prior filed application titled "Bandless Hearing Protector and Method," filed Jun. 26, 2008, which is a continuation-in-part of U.S. Ser. No. 11/799,264 filed Apr. 30, 2007 and U.S. Ser. No. 11/821,391 filed Jun. 22, 2007, all of which are incorporated herein by reference.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A self-conforming sound attenuation earplug comprising:
   a stem made of a stem material and having a stem ear end and an opposite stem user end;
   a first support joined with the stem and made of a deformable-resilient support material and having at least a part of the first support located between the stem ear end and the stem user end, wherein the first support extends radially outward from the stem;
   a shell made of a deformable-resilient shell material and having a tapered exterior that increases in circumference when moving from the stem ear end to the stem user end, the shell engaging at least a portion of the first support and engaging at least a portion of the stem located between the stem ear end and the stem user end, wherein at least a portion of the first support is free from contact with the shell and the first support material is a different type of material than the shell material; and
   a second support joined with the stem, wherein the second support extends radially outward from the stem and the second support is free from contact with the shell; and
   wherein the stem and both the first and second supports are composed of the same type of material.

2. The earplug of claim 1 wherein a space is formed between an inner circumference of the shell and an outer circumference of the stem.

3. The earplug of claim 1 wherein the second support is made of a deformable-resilient second support material.

4. The earplug of claim 1 wherein the shell is located between the first support and the second support.

5. The earplug of claim 1 wherein the shell is located between the first support and the stem user end.

6. The earplug of claim 1 wherein the shell has a portion that is a continuous annular cross section ring and a radial thickness of the ring is between about 1 millimeter and about 8 millimeters.

7. The earplug of claim 6 wherein the radial thickness of the ring is between about 2 millimeters and about 5 millimeters.

8. The earplug of claim 1 wherein the support material is a thermo-plastic elastomer polymeric material.

9. The earplug of claim 1 wherein the shell material is a cellular foam.

10. The earplug of claim 1, wherein the shell comprises a foam material.

11. A self-conforming sound attenuation earplug comprising:
    a stem made of a stem material and having a stem ear end and an opposite stem user end;
    a first support joined with the stem and made of a deformable-resilient support material and having at least a part of the first support located between the stem ear end and stem user end, wherein the first support extends radially outward from the stem;
    at least a second support joined with the stem and made of a deformable-resilient second support material, wherein the second support extends radially outward from the stem and the second support is free from contact with the shell, wherein the stem and both the first and second supports are composed of the same type of material;

a first shell made of a deformable-resilient shell material and having a tapered exterior that increases in circumference when moving from the stem ear end to the stem user end, the first shell engaging at least a portion of the first support and engaging at least a portion of the stem located between the stem ear end and the stem user end, wherein at least a portion of the first support is free from contact with the first shell and the first support material is a different type of material than the shell material; and a second shell made of a deformable-resilient second shell material and having a tapered exterior that increases in circumference when moving from the stem ear end to the stem user end.

12. The earplug of claim 11 wherein the second shell is separated from the first shell by at least one support between the second shell and the shell.

13. The earplug of claim 11 wherein the second shell material is a different type of material than the first shell material.

* * * * *